(12) United States Patent
Burri et al.

(10) Patent No.: US 9,753,046 B2
(45) Date of Patent: *Sep. 5, 2017

(54) SYSTEM AND METHOD FOR LOCATING SAMPLE VESSELS

(71) Applicant: Roche Diagnostics Operations, Inc., Indianapolis, IN (US)

(72) Inventors: Martin Burri, Bettwil (CH); Andreas Eberhart, Oberwil b. Zug (CH); Akihiro Tanji, Kanagawa Pref. (JP)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/728,313

(22) Filed: Jun. 2, 2015

(65) Prior Publication Data

US 2015/0260744 A1  Sep. 17, 2015

Related U.S. Application Data

(63) Continuation of application No. 14/055,266, filed on Oct. 16, 2013, now Pat. No. 9,076,121.

(30) Foreign Application Priority Data

Oct. 24, 2012  (EP) .................................. 12189686

(51) Int. Cl.
*G06F 19/00* (2011.01)
*G06Q 30/00* (2012.01)
(Continued)

(52) U.S. Cl.
CPC .......... *G01N 35/00732* (2013.01); *B01L 9/06* (2013.01); *B01L 99/00* (2013.01);
(Continued)

(58) Field of Classification Search
CPC ......... G06F 19/00; G06F 17/00; G06Q 30/00; G06Q 90/00; G06Q 10/00; G06Q 10/087;
(Continued)

(56) References Cited

U.S. PATENT DOCUMENTS

| 4,857,716 A | 8/1989 | Gombrich et al. |
| 6,170,746 B1 | 1/2001 | Brook et al. |

(Continued)

FOREIGN PATENT DOCUMENTS

| EP | 2299278 A2 | 3/2011 |
| JP | 2004-093518 A | 3/2004 |

(Continued)

*Primary Examiner* — Edwyn Labaze
(74) *Attorney, Agent, or Firm* — Roche Diagnostics Operations, Inc.

(57) ABSTRACT

A system and method for locating sample vessels are presented. The system comprises a holder having an array of positions for holding sample vessels. An information tag is attached to the holder for storing and/or retrieving machine-readable information related to the positions of sample vessels with respect to the array of positions. The system further comprises a handheld device capable of reading information on the information tag. The handheld device has an input for inputting information related to a to-be-located sample vessel and an output for outputting a position of the to-be-located sample vessel with respect to the array of positions based on information stored in the information tag. The method comprises inputting information related to a to-be-located sample vessel into the handheld device, reading information stored in the holder's information tag with the handheld device; and outputting a position of the to-be-located sample vessel.

19 Claims, 4 Drawing Sheets

(51) Int. Cl.
    *G06Q 90/00*         (2006.01)
    *G01N 35/00*         (2006.01)
    *G06Q 10/08*         (2012.01)
    *B01L 9/06*          (2006.01)
    *B01L 99/00*         (2010.01)

(52) U.S. Cl.
    CPC ...... *G06Q 10/087* (2013.01); *B01L 2300/024* (2013.01); *G01N 2035/00782* (2013.01); *G01N 2035/00801* (2013.01); *G01N 2035/00831* (2013.01); *G01N 2035/00851* (2013.01)

(58) Field of Classification Search
    CPC .......... G06Q 20/203; G06K 7/00; G06K 9/22; G06K 19/00
    USPC .............. 235/385, 375, 487, 462.01, 472.01, 235/462.45
    See application file for complete search history.

(56) References Cited

U.S. PATENT DOCUMENTS

| | | | |
|---|---|---|---|
| 6,255,614 B1 | 7/2001 | Yamakawa et al. | |
| 7,992,770 B2 | 8/2011 | Holley | |
| 2004/0100415 A1* | 5/2004 | Veitch | G06K 19/07758 343/850 |
| 2005/0254999 A1 | 11/2005 | Higuchi | |
| 2006/0039834 A1 | 2/2006 | Itoh | |
| 2006/0051239 A1 | 3/2006 | Massaro | |
| 2006/0180659 A1 | 8/2006 | Loffredo et al. | |
| 2006/0283945 A1* | 12/2006 | Excoffier | B01L 3/5457 235/439 |
| 2007/0172396 A1 | 7/2007 | Neeper et al. | |
| 2007/0201025 A1 | 8/2007 | Greenwald | |
| 2009/0048870 A1* | 2/2009 | Godshall | G06Q 50/24 705/3 |
| 2009/0322486 A1* | 12/2009 | Gerstel | B65G 1/1371 340/10.1 |
| 2010/0025464 A1* | 2/2010 | Trueeb | B01L 3/545 235/385 |
| 2010/0238039 A1 | 9/2010 | Tethrake et al. | |
| 2010/0294840 A1 | 11/2010 | Barry | |
| 2010/0322822 A1* | 12/2010 | Fritchie | G01N 35/1009 422/63 |
| 2011/0158850 A1 | 6/2011 | Pedrazzini | |
| 2011/0159578 A1* | 6/2011 | Godsey | G01N 35/1002 435/287.1 |
| 2012/0025985 A1* | 2/2012 | Bolander | G06Q 10/08 340/572.1 |
| 2012/0052560 A1 | 3/2012 | Knight et al. | |
| 2012/0118954 A1 | 5/2012 | Hagen et al. | |
| 2013/0027185 A1 | 1/2013 | Lavi | |
| 2013/0320079 A1* | 12/2013 | Nordin | G06K 5/00 235/375 |
| 2014/0240100 A1* | 8/2014 | Johns | G06K 19/0723 340/10.6 |

FOREIGN PATENT DOCUMENTS

| | | |
|---|---|---|
| JP | 2007-309675 A | 11/2007 |
| JP | 2012-189379 A | 10/2012 |
| WO | 99/30824 A1 | 6/1999 |
| WO | 02/086514 A3 | 10/2002 |
| WO | 2009/002358 A1 | 12/2008 |
| WO | 2009/077465 A1 | 6/2009 |

* cited by examiner

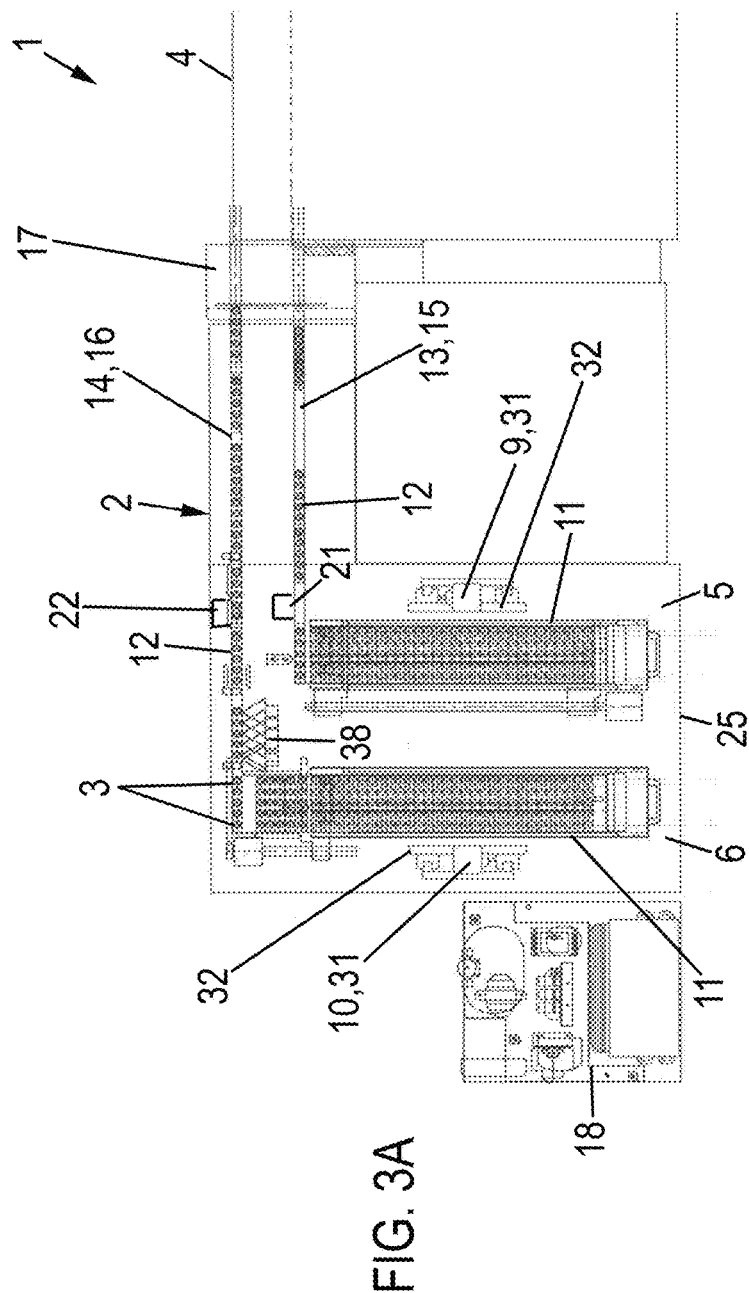
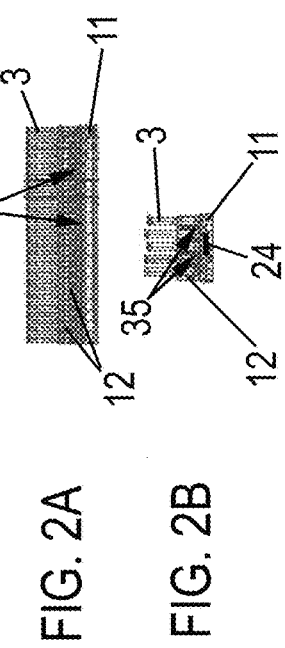
FIG. 3A
FIG. 2A
FIG. 2B

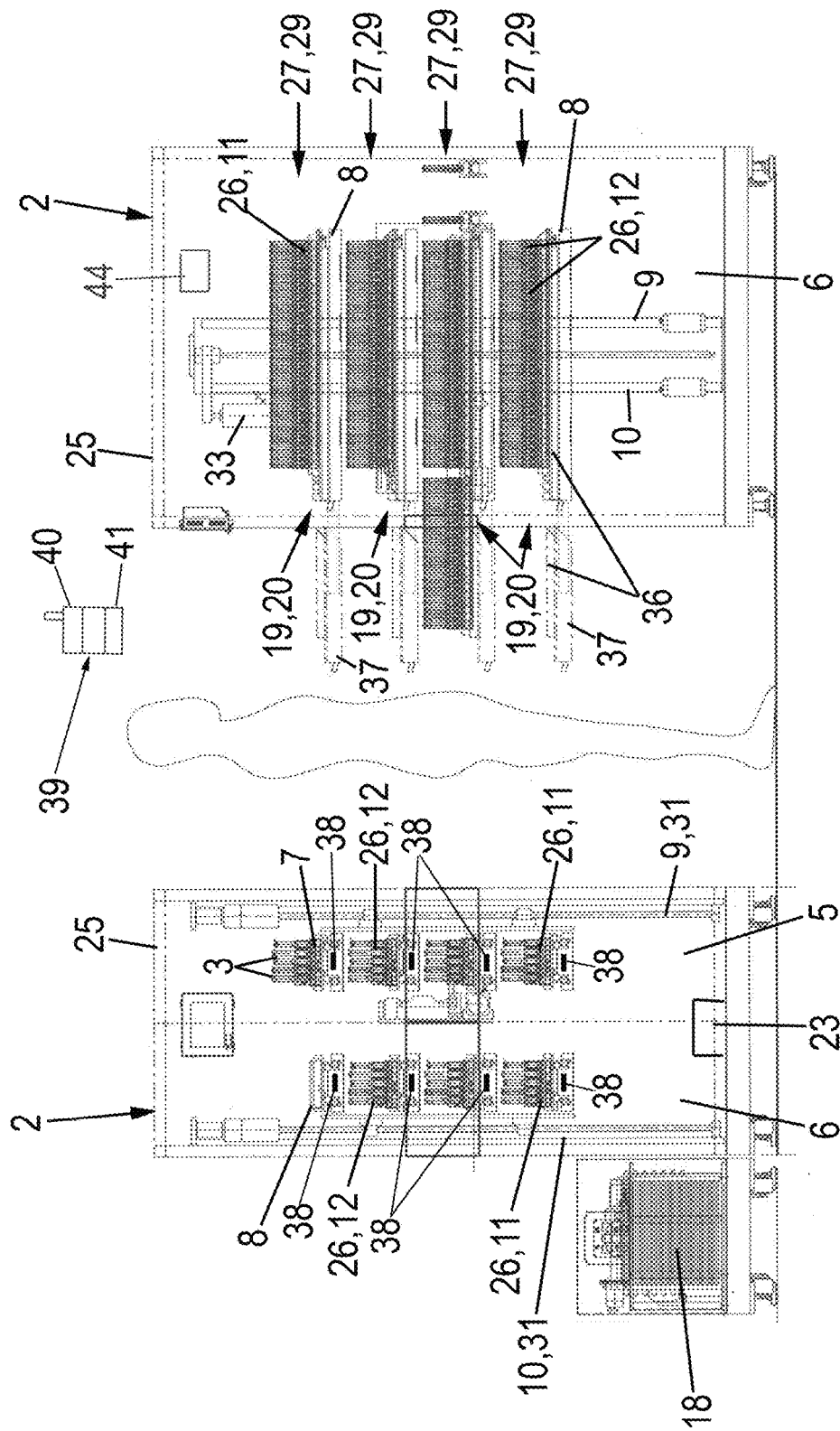

SYSTEM AND METHOD FOR LOCATING SAMPLE VESSELS

CROSS-REFERENCE TO RELATED APPLICATIONS

This application is a continuation of U.S. patent application Ser. No. 14/055,266, filed Oct. 16, 2013, now allowed, which is based on and claims priority to EP 12189686.4, filed Oct. 24, 2012, which is hereby incorporated by reference.

BACKGROUND

The present disclosure generally relates to the field of analytical sample processing and, in particular, to a system and method for locating sample vessels for analytic sample processing.

In automated clinical analyzers, liquid samples, such as bodily fluids, can be tested by various clinical-chemical and immunochemical methods. Modern analyzers typically can be loaded with many samples in a batch-wise manner requiring longer processing times of, for example, hours. In practical use, a situation may arise that a particular sample must be located after having been analyzed and while stored in a suitable, for example, cooled or refrigerated area, for example, for re-testing. When not stored in compartments for the automatic retrieval of samples, the time to access the desired sample can be unacceptably long since each sample vessel has to be checked for identification. On the other hand, fully automated storage solutions may be not suitable or not available in every customer environment.

Therefore, there is a need to locate individual sample vessels quickly with easy access to the samples.

SUMMARY

According to the present disclosure, a system and method for locating sample vessels is presented. The system can comprise at least one vessel holder having an array of vessel positions for holding sample vessels. An information tag can be attached to the vessel holder for storing and/or retrieving machine-readable information related to the positions of sample vessels with respect to the array of vessel positions. The system can further comprise a handheld device capable of reading information provided by the information tag. The handheld device can have an input section for inputting information related to a to-be-located sample vessel and an output section for outputting a position of the to-be-located sample vessel with respect to the array of vessel positions based on information stored in the information tag.

Accordingly, it is a feature of the embodiments of the present disclosure to locate individual sample vessels quickly with easy access to the samples. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 2A-B illustrate depict a longitudinal side view (FIG. 2A) and a front view (FIG. 2B) of the tray provided with plural racks for holding sample vessels of the system of FIGS. 1A-B according to an embodiment of the present disclosure.

FIG. 3A-C illustrate another schematic top view (FIG. 3A) of the system of FIGS. 1A-B illustrating more details, a schematic front view (FIG. 3B) and a schematic side view (FIG. 3C) of the storing/retrieving device of the system of FIGS. 1A-B according to an embodiment of the present disclosure.

DETAILED DESCRIPTION

Figures 1A, 1B:
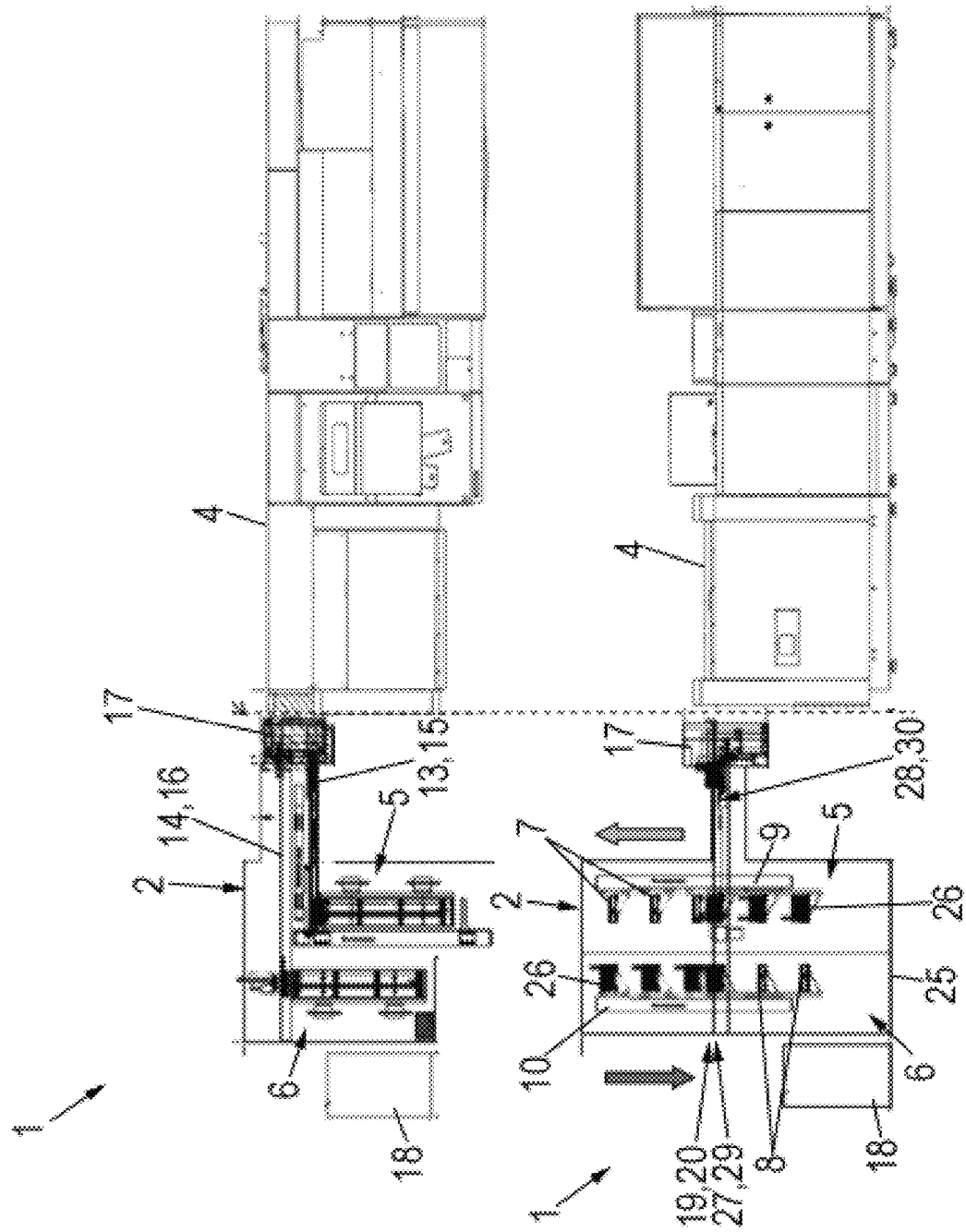
FIGS. 1A-B illustrate schematic top view (FIG. 1A) and a schematic longitudinal side view (FIG. 1B) of a system for processing sample vessels according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

According to a first embodiment, a new system for locating sample vessels is presented. The system can be configured in various ways in accordance with specific demands of the user and, for example, can be used in connection with automated analyzers for analyzing samples by various analytical methods such as, but not limited to, clinical-chemical, immunochemical and biochemical analysis items.

According to one embodiment, the system can include at least one vessel holder having an array of vessel positions for holding sample vessels. As used herein, the term "vessel holder" can relate to any device capable of holding one or more sample vessels for receiving samples in dedicated positions. As used herein, the term "vessel position" can relate to a region of the vessel holder for holding one sample vessel. In one embodiment, the vessel holder can comprise one or more racks, each of which can hold one or more sample vessels, for example, in a linear arrangement. In one embodiment, one or more racks can be located on a tray adapted to arrange one or more racks and/or one or more single vessel holders. The tray can have one or more rack positions for holding racks. As used herein, the term "rack position" can relate to a region of the tray for holding one rack which, in one embodiment, can be adapted to the geometry (outer shape) of the rack, and, in one alternative embodiment, may not be adapted to the geometry of the rack. In one embodiment, the holder can comprise one or more single vessel holders (for example, single tube holders), each of which can hold one sample vessel (for example, a single tube). In one embodiment, the vessel holder can comprise a combination of one or more racks and one more single vessel holders. In one embodiment, one or more racks and one or more single vessel holders can be located on a tray comprising one or more rack positions for holding racks and one or more single vessel holder positions for holding single vessel holders. As used herein, the term "sample vessel" can relate to any device capable of containing one sample. In one embodiment, the sample vessel can be a sample tube.

An information tag can be attached to each vessel holder for storing and/or retrieving machine-readable information related to positions of sample vessels with respect to the vessel positions provided by the vessel holder. In one embodiment, an information tag can be attached to each sample vessel on the vessel holder. In one embodiment, the information tag can be a memory tag. As used herein the term "memory tag" can indicate an information storage device which can be used to store (write) information thereon and to read the stored information. In one embodiment, the memory tag can be selected from an RFID-tag, a magnetic storage tag and a memory chip.

In one embodiment, the vessel holder can have a memory tag, with each sample vessel having a read-only tag. In one embodiment, one or more sample vessels and/or one or more vessel holders respectively can have a read-only tag (without writing function) containing machine-readable information for reading information. In one embodiment, in which the holder can comprise one or more racks and/or one or more single vessel holders (for example, single tube holders) located on a tray, the memory tag can be attached to the tray and/or each rack and/or each single vessel holder and/or each sample vessel. Specifically, the memory tag can be attached to the tray and each sample vessel. Specifically, the memory tag can be attached to the tray. Each sample vessel can have a read-only tag such as, but not limited to, a barcode label. Specifically, the memory tag can be attached to the tray. Each sample vessel and/or each rack and/or each single vessel holder can have a read-only tag such, but not limited to, a barcode label.

The information tag can be used for storing information related to one or more sample vessels. Specifically, the information related to one sample vessel may can comprise a variety of data, for example, sample identity (ID), vessel ID, patient ID, sample date, kind of sample, which analyzes are to be performed or have yet been performed and the like. In one embodiment, information with respect to one sample and sample vessel, respectively, can be stored on an information tag attached to the sample vessel.

Specifically, information contained in an information tag can typically comprise position information. As used herein, the term "position information" can relate to the position of one or more samples vessels on one vessel holder. Since each vessel holder can hold one or more sample vessels in dedicated positions, each sample vessel can be associated with one vessel position so as to obtain a one-to-one relationship between sample vessels and vessel positions on the vessel holder. Since there can regularly be a known one-to-one relationship between samples and sample vessels, the position information can also relate to information of the position of one or more samples on one vessel holder. The term "position information" can further relate to the position of individual vessel holders in the system. The information tag attached to a vessel holder can typically contain the position information of one or more sample vessels on the vessel holder.

Accordingly, in one embodiment, the information tag can be used for storing inventory information. As used herein, the term "inventory information" can relate to the position information of sample vessels. It can also relate to further information, for example, with respect to samples, such as, for example, sample date or patient name. As used herein, the term "inventory" can relate to the inventory information stored as a whole in an information tag. Accordingly, sample vessels and/or vessel holders can readily be located and traced by the inventory.

Accordingly, a newly generated arrangement of sample vessels with respect to the vessel positions of one vessel holder can be stored in the information tag (memory tag) of the vessel holder to be retrieved later for locating individual sample vessels. It, thus, may not be necessary to keep a specific arrangement of sample vessels with respect to the vessel positions of one vessel holder which strongly facilitates sample processing, for example, in a case in which samples are processed in a different manner. In one embodiment, in which one or more sample vessels are put on one rack, each of the one or more sample vessels can remain in a same position with respect to the rack.

In one embodiment, a memory tag for storing and/or retrieving information can be changed to a read-only tag for retrieving information, for example, by fusing a conductor contained in the memory tag. In one embodiment, information contained in a memory tag for storing and/or retrieving information can be secured, for example, by encrypting or by checksums in order to prevent changing and/or reading the information contained therein.

The system can further include a mobile handheld device, capable of reading information provided by the information tag of the vessel holder and sample vessels. The handheld device can have an input section for inputting information related to a to-be-located (i.e., requested) sample vessel and an output section for outputting a position of the to-be-located sample vessel with respect to the array of positions based on the information stored in the information tag. In one embodiment, the handheld device can be programmed by an application for setting up the device to read position information from the information tag of a vessel holder and to output a position of a to-be-located sample vessel based on a request input into the handheld device.

The system of the invention can thus make it possible that requested samples can readily be located with respect to the array of vessel positions of the vessel holder. Accordingly, individual samples can readily be checked with respect to the status of sample processing and/or can easily be handled, for example, for removing samples from any long-time storage compartment such as refrigerators, for example, for re-testing or to remove samples from the system. Hence, a major advantage of the system can be that, in contrast to prior art, the user can need less time to locate a sample, for example, in a long-time storage compartment.

In one embodiment of the system, the output section of the handheld device can graphically display the position of the to-be-located sample vessel with respect to the array of vessel positions of one vessel holder, for example, by displaying the array of vessel positions and highlighting the position of the to-be-located sample vessel. Accordingly, the location of the requested sample vessel can readily and quickly be recognized by the user.

In one embodiment of the system, the output section of the handheld device can alphanumerically output the vessel position of the to-be-located sample vessel with respect to the array of vessel positions. This can also allow a requested sample vessel to be easily and quickly located relative to the vessel positions of the vessel holder.

In one embodiment of the system, the output section of the handheld device can display a direction towards the position of the to-be-located sample vessel relative to an orientation of the handheld device. Accordingly, a user can immediately be directed towards the requested sample vessel to quickly access the sample vessel.

In one embodiment, the system can further comprise a first storage compartment comprising a plurality of first storage sections disposed on different levels for storing of vessel holders and a second storage compartment comprising a plurality of second storage sections disposed on different levels for storing of vessel holders. The system can further comprise at least one analyzer for analyzing samples contained in sample vessels and a reader/writer for reading information provided by information tags of vessel holders and/or writing information including position information of sample vessels with respect to the vessel positions into the information tags of vessel holders. The system can further comprise a controller to operate the reader/writer for writing information including position information of sample vessels with respect to the vessel positions into the information tag of a vessel holder, for example, when located in the second storage compartment, prior to removing the vessel holder from the second storage compartment. In one embodiment, the reader/writer can be located in the second storage compartment. The handheld device can be neither part of nor contained in the first or second storage compartments.

In one embodiment, the system can further comprise a first translating mechanism for vertically translating the first storage sections so as to translate one storage section at a time to a loading level of a loading zone for loading vessel holders into the first storage compartment and to translate one storage section at a time to a handing-in level of a handing-over station for handing in vessel holders to the analyzer for analyzing the samples, a second translating mechanism for vertically translating the second storage sections so as to translate one storage section at a time to a handing-out level of the handing over station and to translate one storage section at a time to an unloading level of an unloading zone for unloading vessel holders from the second storage compartment, a first transport mechanism comprising a first conveyor for transporting vessel holders from a first storage section at the handing-in level to the handing-over station, a second transport mechanism comprising a second conveyor for transporting vessel holders from the handing-over station to a second storage section at the handing-out level, and a handing-over station for handing over vessel holders from the first storage compartment to the analyzer and from the analyzer to the second storage compartment.

In one embodiment, the handheld device can be set up to automatically read information from the information tag of a vessel holder and/or sample vessels outside the first or second storage compartments. In one embodiment, the handheld device can be set up to write information comprising position information into the information tag of a vessel holder outside the first or second storage compartments after removing one or more sample vessels from the vessel holder for updating position information stored in the information tag of the vessel holder.

In one embodiment, the first and/or second storage compartment can have a cooled environment for vessel holders.

In one embodiment, the system can comprise a sorting device for sorting sample vessels into the array of positions, with the sorting device coupled to a writer set up to write information comprising position information related to the positions of the sorted sample vessels with respect to the array of positions into the information tag of the vessel holder. Accordingly, a newly generated arrangement of sample vessels with respect to the vessel positions of the vessel holder can be stored in the information tag of the vessel holder to be retrieved later for locating individual sample vessels.

According to another embodiment, an automated method of locating sample vessels is proposed. The method can be configured in various ways in accordance with specific demands of the user and, such as, for example, it can be used in connection with automated analyzers related to various analytical methods. Specifically, the method of the invention can be used in a system as described above.

The method can comprise inputting information related to a to-be-located/requested sample vessel into a handheld device capable of reading information stored in an information tag for storing and/or retrieving machine-readable information.

The method can comprise reading information with the handheld device. The information can be stored in an information tag attached to a vessel holder having an array of positions for holding sample vessels and can be related to positions of sample vessels with respect to the array of vessel positions.

The method can comprise outputting a position of the to-be-located sample vessel with respect to the array of positions on the handheld device based on position information stored in the information tag.

In one embodiment, inputting information related to a to-be-located sample vessel can comprise inputting an identification of the to-be-located sample vessel and/or an identification of a person from whom sample contained in the sample vessel can be drawn.

In one embodiment, outputting the position of the individual sample vessel with respect to the array of positions can comprise graphically displaying and/or alphanumerically outputting the position of the to-be-located sample vessel with respect to the array of positions of the vessel holder.

In one embodiment, the method can comprise writing information related to positions of sample vessels with respect to the array of vessel positions of the vessel holder into the information tag.

In one embodiment, the method can comprise reading information from information tags attached to sample vessels. The information can be related to positions of sample vessels with respect to the array of vessel positions and writing information comprising position information into an information tag attached to the vessel holder after removing one or more sample vessels from the vessel holder for updating information related to positions of sample vessels with respect to the array of vessel positions stored in the information tag. Specifically, in one embodiment, the method can comprise reading information comprising position information from information tags attached to sample vessels, for example, on a vessel holder placed in long-term storage such as a refrigerator, and, for example, after removing of one or more sample vessels from the vessel holder, writing information comprising position information into an information tag attached to the vessel holder so as to update the inventory of the vessel holder. As used herein, the term "update" can relate to a change of the information comprising position information stored in the information tag of the vessel holder with respect to samples (or sample vessels) which have been removed. The position of the remaining sample vessels can also be changed and the changes can be updated in the information tag.

In one embodiment, information contained in the information tag can be locked after writing into the information tag so as to protect the content and to prevent access. In one embodiment, an information tag for storing and retrieving of information can be changed to a read-only information tag for retrieving information after writing the information thereon so that the information tag can only be used to read information stored thereon without a possibility to change the stored information. Accordingly, information can readily be kept on the information tag. In one embodiment, information stored on the information tag can be protected, e.g., by encrypting or by checksums in order to prevent changing and/or reading of the information.

In one embodiment, the method can comprise sorting sample vessels into the array of positions of the vessel holder and writing information related to positions of the sorted sample vessels with respect to the array of positions into the information tag of the vessel holder.

In one embodiment, the method can comprise displaying a direction towards the position of the to-be-located sample vessel relative to an orientation of the handheld device.

Referring initially to FIGS. 1A-B, FIGS. 1A-B illustrating a top view (FIG. 1A) and a side view (FIG. 1B) of an automated system for locating sample vessels generally referred to as reference numeral 1. Specifically, the system 1 can include an automated storing/retrieving device 2 for storing and retrieving of sample vessels 3 for containing samples. The storing/retrieving device 2 can be operatively coupled to an automated analyzer 4 for analyzing samples contained in the sample vessels 3.

The storing/retrieving device 2 can include a housing 25 enclosing two storage compartments 5, 6 for storing sample vessels 3. Specifically, a first storage compartment 5 can comprise a plurality of first storage sections 7 disposed on different, vertically spaced apart levels for storing of vessel holders 26 and a second storage compartment 6 adjacent and side-to-side to the first storage compartment 5 can comprise a plurality of second storage sections 8 disposed on different, vertically spaced apart levels for storing of vessel holders 26. Each vessel holder 26 can hold a plurality of sample vessels 3.

In the storing/retrieving device 2, each of the storage compartments 5, 6 can be operatively coupled to a translating mechanism 9, 10, respectively with the first storage compartment 5 coupled to a first translating mechanism 9 for vertically translating the first storage sections 7 and the second storage compartment 6 coupled to a second translating mechanism 10 for vertically translating the second storage sections 8. The first and second translating mechanisms 9, 10 can be independently operated with respect to each other.

In the first storage compartment 5, one first storage section 7 at a time can be vertically translated to a loading level 27 of a loading zone 19 for loading vessel holders 26 into the first storage compartment 5. As illustrated, in one embodiment, the loading level 27 can be located in a middle portion of the housing 25 but can also be located in an upper portion and/or a lower portion of the housing 25. In the first storage compartment 5, one first storage section 7 at a time can be vertically translated to a handing-in level 28 for handing in vessel holders 26 from the first storage section 7 to a handing-over station 17 for handing over vessel holders 26 to the analyzer 4. In the second storage compartment 6, one second storage section 8 at a time can be vertically translated to a handing-out level 30 of the handing-over station 17 for handing out vessel holders 26 from the handing-over station 17 to the second storage section 8. Furthermore, in the second storage compartment 6, one second storage section 8 at a time can be vertically translated to a unloading level 29 of a unloading zone 20 for unloading vessel holders 26 from the second storage compartment 6.

The first and second translating mechanisms 9, 10 can be operated independently from each other so that the first storage sections 7 can be vertically translated without simultaneously vertically translating the second storage sections 8, and vice versa. As illustrated in FIG. 3A, in one embodiment, the first and second translating mechanisms 9, 10, respectively, can be constructed as geared elevators, each of which comprising a vertical rod 31 connected to a carrier 32 movably fixed to the rod 31, with the storage sections 7, 8 mounted to the carrier 32. In one embodiment, the carrier 32 can be in threaded engagement with the rod 31 so that the carrier 32 can be moved upwards or downwards by rotating the rod 31 along its longitudinal axis. As illustrated in FIG. 3C, an electric motor 33 can be used to rotate the rod 31.

With continued reference to FIGS. 1A-B, in the system 1, the storing/retrieving device 2 can include a first transport mechanism 13 operatively coupled to the first storage compartment 5 can comprise a first conveyor 15 for transporting vessel holders 26 from a first storage section 7 at the handing-in level 28 to the handing-over station 17. The first conveyor 15 can, for example, be a unidirectional conveyor for transporting vessel holders 26 from the first storage 7 to the handing-over station 17 but not in the reverse direction. In one embodiment, the first conveyor 15 can have a decapping unit 21 for decapping sample vessels 3 passing by.

The storing/retrieving device 2 can include a second transport mechanism 14 that can be independently operable from the first transport mechanism 13. The second transport mechanism 14 can be operatively coupled to the second storage compartment 6 and can comprise a second conveyor 16 in parallel to the first conveyor 15 for transporting vessel holders 26 from the handing-over station 17 to a second storage section 8 at the handing-out level 30. The second conveyor 16 can, for example, be a unidirectional conveyor for transporting vessel holders 26 from the handing-over station 17 to the second storage section 8 but not in the reverse direction. In one embodiment, the second conveyor 16 can have a recapping unit 22 for recapping sample vessels 3 passing by. The first and second conveyors 15, 16, respectively, can, for example, be a driven conveyor belt which is known in the art, so that it is not necessary to further elucidate it.

In order to transport vessel holders 26 from the first storage section 7 at the handing-in level 28 to the first conveyor 15 and from the first conveyor 15 to the handing-over station 17, the first transport mechanism 13 can comprise moving devices such as, but not limited to, pushers and/or grippers capable of pushing and gripping, respectively, the vessel holders 26. Analogously, in order to transport vessel holders 26 from the handing-over station 17 to the second conveyor 16 and from the second conveyor 16 to the second storage section 8 at the handing-out level 30, the second transport mechanism 14 can comprise moving devices such as, but not limited to, pushers and/or grippers capable of pushing and gripping, respectively, the vessel holders 26.

Accordingly, the storing/retrieving device 2 can be used for storing vessel holders 26 containing to-be-processed samples in various levels in the first storage compartment 5 and for transporting vessel holders 26 to the handing-over station 17 for handing over to the analyzer 4 for analyzing samples contained in the sample vessels 3. Specifically, due to the vertical arrangement of the first storage sections 7 on various levels, a comparably large number of samples can be stored in the first storage compartment 5. Samples which have already been processed by the analyzer 4 can be handed over to the handing-over station 17 so as to be transported to and stored in various levels in the second storage compartment 6 to be unloaded upon demand. Due to the vertical arrangement of the second storage sections 8 on various levels, a comparably large number of processed samples can be stored in the second storage compartment 6. Samples, which have by-passed the analyzer 4, can also be loaded into the second storage compartment 6.

For storing samples in the first and second storage compartments 5, 6, respectively, in one embodiment, the storage compartments 5, 6 can be operatively coupled to at least one cooling device 23, such as, but not limited to, a fluidic cooling device comprising a cooled fluid and one or more Peltier devices for actively cooling samples contained therein. As is known in the art, Peltier devices can function as heat pumps to absorb or generate heat according to the direction of current applied. Accordingly, samples can be stored in the storage compartments 5, 6 for a longer period without deterioration of the samples.

With reference to FIGS. 2A-C, in one embodiment, each vessel holder 26 can include an elongated tray 11 having a plurality of rack/holding positions 34, each of which can hold one rack 12. In one embodiment, the tray 11 can have 20 or more rack positions 34 in parallel arrangement with respect to each other. Those of skill in the art can appreciate that any other number of rack positions 34 and arrangement thereof can be envisaged according to the specific demands of the user. The racks 12 can readily be inserted into the rack positions 34 so as to be held therein and can be removed from the tray 11 by sliding them out of the rack positions 34.

In one embodiment, the tray 11 can have one or more single tube holder/holding positions, each of which can hold one single tube holder. Accordingly, single tube holders can readily be inserted into the single tube holder positions so as to be, for example, fixedly held therein and can be removed from the tray 11 by sliding them out of the single tube holder positions.

In one embodiment, the tray 11 can have one or more rack positions 34, each of which can hold one rack 12 and one or more single tube holder positions, each of which can hold one single tube holder. As used herein, the term "rack" can also be identified as single tube holder.

Each elongated rack 12 can have a plurality of vessel positions 35, each of which can hold one sample vessel 3. As illustrated, in one embodiment, the rack 12 can have five vessel positions 35 serially arranged with respect to each other. Those of skill in the art can appreciate that any other number of vessel positions 35 and arrangement thereof can be envisaged according to the specific demands of the user. The sample vessels 3 can be inserted into the vessel positions 35 and can be removed from the rack 12 by sliding them out of the vessel positions 35. On the tray 11, the racks 12 can be in parallel arrangement with respect to each other, with the vessel positions 35 of each rack 12 arranged along a row perpendicular to the elongation of the tray 11. Each single tube holder can have one tube position for holding one sample tube.

As further illustrated, in one embodiment, the sample vessels 3 can be configured as top-closed tubes, each of which can have a cap pressed into the tube for fixing. The tubes can be inserted into the rack positions 34 in an upright position. The caps can be removed from the tubes by the decapping unit 21 arranged at the first conveyor 15 and can be recapped by the recapping unit 22 arranged at the second conveyor 16. The vessel holders 26 other than top-closed tubes can be used, such as, but not limited to, sample cups.

As further illustrated in FIGS. 2B-C, in the system 1, each vessel holder 26 can have a memory tag 24 for storing/retrieving machine-readable information. In one embodiment, the memory tag 24 can be an RFID-chip allowing for a contactless writing and reading of information via radio signals typically in proximity to the memory tag 24 (i.e., near-field transmission).

With continued reference to FIGS. 2B-C, in one embodiment, the tray 11 can have the memory tag 24 that, for example, can be attached to a front-side of the tray 11. Specifically, the memory tag 24 can be used to store a tray ID, rack IDs, sample vessel IDs and/or sample IDs. Specifically, the memory tag 24 can be used to retrieve position information of sample vessels 3 with respect to the vessel positions 35 of the racks 12 on the tray 11. Each sample vessel 3 can also have a memory tag 24 for storing/retrieving machine-readable information.

With continued reference to FIG. 2C, in one embodiment, each sample vessel 3 can have a read-only tag 40 for retrieving (but not writing) machine-readable information such as, but not limited to, a barcode label indicating a sample ID and sample vessel ID, respectively. In one embodiment, each rack 12 can have a read-only tag 40 for retrieving (but not writing) machine-readable information such as, but not limited to, a barcode label indicating a rack ID.

With reference to FIGS. 3A-C illustrating a system 1 for locating sample vessels using trays 11 as illustrated in FIGS. 2A-C, in one embodiment, each of the first and second storage compartments 5, 6 can comprise four first and four second storage sections 7, 8, respectively, which can be disposed in different levels vertically stacked one upon the other. Each storage section 7, 8 can be loaded with one tray 11, for example, having 20 or more racks 12 for holding sample vessels 3. A lock can be used for locking/unlocking the tray 11 on the storage section 7, 8.

In one embodiment, each storage section 7, 8 can comprise a pair of guiding rails 36 slidably supporting one tray 11 so that the tray 11 can readily be moved along the guiding rails 36 to be inserted in or removed from the first and second storage compartments 5, 6, respectively.

With reference to FIG. 3C, in one embodiment, the housing 25 can comprise four hinged doors 37 on various levels, each of which defining one loading zone 19 and one unloading zone 20 on a same level. The doors 37 can be hinged down or up to provide access to or close the corresponding loading zone 19 of the first storage compartment 5 and unloading zone 20 of the second storage compartment 6. The number of doors 37 and the corresponding number of loading/unloading zones 19, 20 can vary according to the specific demands of the user. Particularly, only one door 37 on one level can be envisaged for loading/unloading of racks 12 and/or trays 11.

As further illustrated, the inner side of each door 37 can also have guiding rails 36 so that a tray 11 can be put on the hinged-down door 37 to be slidably moved into the storage section 7, 8 or pulled out from the storage section 7, 8. Accordingly, the trays 11 can readily be inserted in and removed from the first and second storage compartments 5, 6, respectively, through the loading zones 19 and/or unloading zones 20. In one embodiment, the first and/or second storage sections 7, 8 respectively can be insertable in and removable from the first and second storage compartments 5, 6, respectively, through the loading zones 19 and/or unloading zones 20.

In the storing/retrieving device 2, the first storage sections 7 can be lifted up or down so as to position the first storage sections 7 on the loading levels 27 for loading with racks 12 (in case empty or partially loaded trays 11 are already present on the first storage sections) or trays 11. Each tray 11 can be vertically translated to the handing-in level 28 for sequentially handing in racks 12 to the handing-over station 17 for handing over racks 12 holding sample vessels 3 containing to-be-processed samples to the analyzer 4. For example, by use of grippers/pushers, the racks 12 (and/or single tube holders) can sequentially be transported on the first conveyor 15 to be transported from the first storage section 7 to the handing-over station 17.

Furthermore, the second storage sections 8 can be lifted up or down so as to position one tray 11 that is empty or partially filled with racks 12 at a time on the handing-out level 30 for handing out racks 12 from the handing-over station 17 to the tray 11. For example, by use of grippers/pushers, the racks 12 (and/or single tube holders) can sequentially brought on/removed from the second conveyor 15 to be transported in-line from the handing-over station 17 to the tray 11. Each rack-loaded tray 11 can then be lifted up or down so as to position it on one unloading level 29 for removing racks 12 and/or trays 11 from the second storage compartment 6.

In order to control the various workflows, the storing/retrieving device 2 can further include a controller 18 to operate the first translating mechanism 7 to translate a first storage section 7 one at a time to one loading level 27 for loading of racks 12 or rack-loaded trays 11 into the first storage compartment 5 and for translating rack-loaded trays 11 one at a time to the handing-in level 27, the first transport mechanism 13 for transporting racks 12 from the tray 11 on the handing-in level 27 to the handing-over station 17, the second translating mechanism 10 for translating empty or partially loaded trays 11 in the second storage compartment 6 one at a time to the handing-out level 30, the second transport mechanism 14 for transporting racks 12 from the handing-over station 17 to the tray 11 on the handing-out level 30 and the second translating mechanism 10 for translating rack-loaded trays 11 one at a time to one unloading level 29 for unloading of racks 12 or rack-loaded trays 11 from the second storage compartment 6.

The controller 18 can include a database for reading/writing (storing) inventory information, for example with respect to individual sample vessels 3, that is to say, position information of sample vessels 3 on a vessel holder 26 with respect to the vessel positions of the vessel holder 26 as given by the racks 12 and/or single tube holders on a tray 11. The data base can also contain inventory information of racks 12 and trays 11, e.g., with respect to the first and second storage sections 7, 8.

In one embodiment, the controller 18 can control a loading mode, for example, initiated by user interaction in which the first transport mechanism 13 can be operated to pause transporting of racks 12 from the first storage sections 7 to the handing-over station 17 and the first translating mechanism 9 can be operated to translate the first storage sections 7 to the loading levels 27 for loading with racks 12 or rack-loaded trays 11. The loading mode can, for example, be performed in parallel to vertically translating the second storage sections 8 one at a time to the handing-out level 30, transporting racks 12 from the handing-over station 17 to the second storage section 8 at the handing-out level 30 and vertically translating the second storage sections 8 to the unloading levels 29 for unloading of racks 12 or rack-loaded trays 11.

In one embodiment, the controller 18 can control a unloading mode, for example, initiated by user interaction in which the second transport mechanism 14 can be operated to pause transporting of racks 12 from the handing-over station 17 to the second storage sections 8 and the second translating mechanism 10 can be operated to translate the second storage sections 8 to the unloading levels 29 for unloading of racks or rack-loaded trays 11 from the second storage compartment 6. The unloading mode can, for example, be performed in parallel to vertically translating the first storage sections 7 to the loading levels 27 for loading of racks 12 or rack-loaded trays 11, vertically translating the rack-loaded trays 11 one at a time to the handing-in level 28 and transporting racks 12 to the handing-over station 17.

With reference to FIG. 3C, the storing/retrieving device 2 can have a panel 39 with an input for inputting information such as a sample ID (ID=identification) and with an output for outputting information, for example, regarding a specific status of the storing/retrieving device 2 and/or inventory information with respect to individual sample vessels 3 and samples, respectively, contained in the data base.

With continued reference to FIG. 3A, the storing/retrieving device 2 can further include a reader/writer 38 arranged at the second conveyor 16 close to the second storage compartment 6. The reader/writer 38 can read machine-readable information provided by memory tags 24 and read-only tags 40 respectively attached to the sample vessels 3 and racks 12, such as, but not limited to, barcode labels indicating sample IDs and sample vessel IDs, respectively, and rack IDs. Accordingly, an identity of each sample and/or sample vessel 3 and/or rack 12 passing the reader/writer 38 can be determined.

The reader/writer 38 can further assign the information read from the sample vessels 3 of one rack 12 concerning the sample IDs to the vessel positions 35 of the rack 12. Accordingly, samples and sample vessels 3, respectively, held by one rack 12 passing the reader/writer 38 can be mapped with respect to the vessel positions 35 of the rack 12. Hence, individual samples and sample vessels 3, respectively, can be allocated to the vessel positions 35 of the rack 12 so as to provide inventory information. Furthermore, e.g. based on inventory information, the controller 18 can determine the position of the racks 12 loaded on the tray 11 at the handing-out level 30 so that the sample vessels 3 loaded on the tray 11 can be mapped with respect to the array of vessel positions 35 as given by the racks 12 on the tray 11.

Furthermore, the controller 18 can operate the reader/writer 38 to write the complete position information of samples and sample vessels 3, respectively, into the memory tag 24 of the tray 11. Accordingly, the memory tag 24 can contain position information of each sample vessel 3 on the tray 11 with respect to the array of vessel positions 35 provided by the racks 12 on the tray 11. The position information of an individual sample vessel 3 can, e.g., be indicated by the rack position 34 carrying the rack 12 of the sample vessel 3 and the vessel position 35 of the rack 12 holding the sample vessel 3.

In one embodiment of the system 1, there can be no pre-defined/predetermined sequential arrangement of sample vessels 3 related to the vessel positions 35 of individual racks 12. Similarly, there can neither be a pre-defined order of racks 12 related to the rack positions 34 of individual trays 11 nor any assignment of racks 12 to individual trays 11. Since the sample vessels 3 carry labels for identifying individual sample vessels 3 and samples contained therein, respectively, the samples can readily be assigned to test results of the analyzer 4.

Typically, each tray 11 in the second storage compartment 6 can usually carry racks 12 that have not been on one tray 11 in the first storage compartment 5. In other words, racks 12 on one tray 11 in the first storage compartment 5 usually can be distributed over plural trays 11 in the second storage compartment 6. This can, for example, be a consequence of the fact that racks 12 may contain samples supposed to be processed in a different manner so that racks 12 from one tray 11 of the first storage compartment 5 can leave the analyzer 4 in an outgoing sequential arrangement that can be different from an ingoing sequential arrangement for supplying the analyzer 4 with these racks 12.

With reference to FIG. 3B, in one embodiment, one reader/writer 38 can be positioned in each unloading zone 20 of the second storage compartment 6 for reading information from memory tags 24 and/or read-only tags and writing information into the memory tags 24. Specifically, the controller 18 can operate the reader/writer 38 to read information from read-only tags attached to sample vessels 3 on one tray 11 so as to identify samples and/or sample vessels 3 and to write position information/inventory information with respect to the vessel positions 35 as given by the racks 12 into the memory tag 24 of the tray 11. Accordingly, inventory information can be stored/changed before removing the tray 11, individual sample racks 12 and/or sample vessels 3 from the second storage compartment 6. The controller 18 can also be used to write inventory information into the controller data base.

With continued reference to FIGS. 3B-C, in one embodiment, one reader/writer 38 can be positioned in each loading zone 19 of the first storage compartment 5 for reading information from memory tags 24 and/or read-only tags and writing information into the memory tags 24. Specifically, the controller 18 can operate the reader/writer 38 to read information from read-only tags attached to sample vessels 3 on one tray 11 so as to identify samples and/or sample vessels 3 and to write position information/inventory information with respect to the vessel positions 35 as given by the racks 12 into the memory tag 24 of the tray 11. Specifically, identification information can be read from the labels of the sample vessels 3 so as to assign the identification information to the vessel positions 35 of individual racks 12 on a tray 11. The controller 18 can also be used to write the inventory information into the controller data base.

In one embodiment, related to providing a sorting device for sorting sample vessels 3 with respect to vessels positions 35 of one rack 12, the sorting device can be coupled to a reader/writer so as to read machine-readable information provided by the labels of the sample vessels 3, can assign the identification information read from the sample vessels 3 to the vessel positions 35 of the rack 12 and can write this information on the tray 11 supporting the rack 12.

In the following, exemplary use cases of the system 1 are described. In a first exemplary use case ("loading samples"), the user can load samples into the first storage compartment 5 while the analyzer 4 can be in operation. Specifically, the user can push a load button of the panel 39 resulting in that the storing/retrieving device 2 can pause handing-in of racks 12 to the handing-over station 17. Furthermore, the storing/retrieving device 2 can automatically detect the next loadable (empty or partly filled) tray 11 and can move this to one loading level 27. The user can then open the door 37 so as to have access to the loading zone 19. In case the user wants to select a different tray 11, this can, e.g., be done by manually inputting "up" or "down" information on the panel 39 until the desired tray 11 has reached the loading zone 19. The user can then open the opens lock of the tray 11 in the loading zone 19, and as a result, e.g., an LED can change color, e.g., to green indicating that the tray 11 in the loading zone 19 can be accessible. The user can then slide the respective tray 11 out of the loading zone 19, fill it with racks 12 and slide the rack-filled tray 11 in. The racks 12 can also be loaded on the tray 11 in the loading zone 19. The user can then close the lock of the tray 11 so that the color of the LED changes, e.g., to red indicating a tray 11 in operation (not accessible). The user can then close the door 37 of the loading zone 19 and the system 1 can start its operation mode for testing the samples loaded into the first storage compartment 5. In parallel, handing-out of racks 12 from the handing-over station 17 to the second storage section 8 at the handing-out level 30 and/or unloading of sample vessels 3 from the second storage sections 8 can remain in operation. Likewise, any system alarm and error surveillance (e.g. temperature control) can remain in operation. Furthermore, an inventory management including registration of rack IDs and/or sample IDs along the second conveyor 16 can remain in operation. In the first storage compartment 5, sample IDs and/or vessel IDs can be read from read-only tags on sample vessels 3, followed by writing inventory information into the memory tag 24 of the tray 11 and/or into the data base of the controller 18.

In a second exemplary use case ("unloading samples"), the user can unload trays 11 from the second storage compartment 6 while the analyzer 4 can be in operation. Specifically, the user can push an unload button of the panel 39 resulting in that the storing/retrieving device 2 can pause handing-out of racks 12 from the handing-over station 17 to the second storage section 8 at the handing-out level 30. Furthermore, the storing/retrieving device 2 can automatically detect the next fully or partially loaded tray 11 and move this to one unloading level 29. The user can then open the door 37 to have access to the corresponding unloading zone 20. In case the user wants to select a different tray 11, this can, e.g., be done by manually inputting "up" or "down" information on the panel 39 until the desired tray 11 has reached the unloading level 29. The user can then open a lock of the tray 11 in the unloading zone 20. The system can then write/read (for confirmation) logistic information (tray ID, sample ID, position) into/from the memory tag of the tray 11 in the unloading zone. After confirmation of the tray logistic information, an LED can change color to, e.g., green indicating the accessible tray 11. The user can then slide the respective tray 11 out to unload with the racks 12. The tray 11 can then be slide in again. The user can then close the lock of the tray 11 resulting in changing the color of the LED, e.g., to red indicating the tray 11 in operation (not accessible). The user can then input "up" or "down" information to select another tray 11 to be vertically translated to the unloading zone 20 to be unloaded. Then, the user can close the door 37 of the unloading zone 20 and the system 1 can start its operation mode for transporting sample racks 12 into the second storage compartment 6. In parallel, handing-in of racks 12 to the handing-over station 17 and/or loading of racks 12 and/or trays 11 into first storage compartment 5 can remain in operation. Likewise, any system alarm and error surveillance (e.g. temperature control) can remain in operation. In the second storage compartment 5, sample IDs and/or vessel IDs can be read from read-only tags on sample vessels 3, followed by writing inventory information into the memory tag 24 of the tray 11 and/or controller data base before unloading.

A third exemplary use case ("routine operation") includes various procedures. In a first procedure ("continuous operation"), the systems 1 can detect rack-loaded trays 11 in the first storage compartment 5, transport one or more rack-loaded trays 11 sequentially to the handing-in level 28, transport racks 12 from the first storage section 7 at the handing-in level 28 to the first conveyor 15 and transport racks 12 from the first conveyor 15 to the handing-over station 17. Furthermore, the system 1 can detect empty or partially loaded trays 11 in the second storage compartment 6, transport one or more empty or partly rack-loaded trays 11 sequentially to the handing-out level 30, transport racks 12 from the handing-over station 17 to the second conveyor 16 and transport racks 12 from the second conveyor 16 to the second storage section 8 at the handing-out level 30. Furthermore, the system 1 can detect empty or partially rack-loaded trays 11 in the first storage compartment 5 and move it to one loading zone 19, and, can detect full or partially rack-loaded tray 11 in the second storage compartment 6 and move it to one unloading zone 20. For unloading trays 11, the system 1 can write/read logistic information (tray ID, sample ID, position) into the memory tag 24 of the tray 11.

In a second procedure ("loading operation"), subsequent racks 12 on one tray 11 can be transported on the first conveyor 15 so as to move the racks 12 to an in-gate of the handing-over station 17. Optionally the rack-ID and sample IDs on the rack 12 can be recognized and/or confirmed to allow inventory management of stored samples before feeding into the analyzer. The system can acknowledge and accept transfer into the in-gate of the handing-over station 17.

In a third procedure ("unloading operation"), subsequent racks 12 can be transported into an out-gate of the handing-over station 17 and then can be pushed on the second conveyor 16 to move the racks 12 to the second storage section 8 at the handing-out level 30. Optionally the rack ID and sample IDs can be recognized. Optionally the rack-ID and sample IDs can be recognized and/or confirmed to allow inventory management of stored samples before feeding into the analyzer. Subsequent racks 12 can be pushed from the second conveyor 16 to the tray 11 in the handing-out level 30. Before unloading, the tray inventory information from the controller system data base/storage for inventory information can be optionally written before handing-out can be allowed.

In a fourth procedure ("temperature control"), the temperature of the system 1 can be controlled, and, if the temperature is outside pre-determinable specifications, an error/alarm can be initiated.

In a fifth procedure ("status control"), the system status can be checked and displayed on the panel 39, e.g., by an icon, color code, or flashing rotating light. The number of full trays 11 (to be unloaded) or empty trays 11 (to be loaded) can be displayed. In case the system status is outside of pre-determined specifications, an error/alarm can be initiated.

In a fourth exemplary use case ("search sample ID"), the user can input a rack and/or sample ID on the panel 39. The controller 18 can then search if the input ID is in the inventory, and, if in inventory, the controller 18 can acknowledge this to the user on the panel 39, including location and interactive user workflow to ask for access to the sample. If the user selects retrieval, the system can detect a tray 11 and can move this tray 11 to one unloading level 29. The user can then open the door 37 of the corresponding unloading zone 20 and can open the lock of the tray 11. The storing/retrieving device 2 can write/read logistic information (tray ID, sample ID, position) into/from the memory tag 24 of the tray 11 or from the controller database inventory. After confirmation of the logistic information, the system can switch the LED to green to indicate that the tray 11 can be accessible. The user can then slide the tray 11 out to remove the desired rack 12 and/or sample. The user can then acknowledge retrieval. The user can then slide the tray 11 back and can close the lock of the tray resulting in switching the LED to red (tray 11 in operation, not accessible). The user can then close the door 37 of the unloading zone 20 and the system can start the operation mode. In parallel, the loading/unloading process can remain in operation. Likewise, any system alarm and error surveillance (e.g. temperature control) can remain in operation.

Accordingly, when unloading a tray 11 from the second storage compartment 6, inventory information with respect to sample vessels 3 on the tray 11 can be written into the memory tag 26 of the tray 11. Furthermore, sample-IDs, rack-IDs and information concerning the time of removing the tray 11 from the second storage compartment 6 can be written on the memory tag 24. Accordingly, samples can be manually or automatically disposed after elapse of a pre-determined period of time.

Furthermore, in case a sample vessel 3 is to be located within the first and second storage compartments 5, 6, respectively, and/or within the analyzer 4, the sample-ID and/or sample vessel-ID can be input by the panel 39. The controller can output the position of sample vessel 3 on the panel 39 based on inventory information, e.g., contained in the controller 18 data base. Accordingly, the user can get information about the location of the sample vessel 3, e.g., using a menu displayed by the panel 39.

With reference to FIG. 3C, the system 1 for processing sample vessels 3 can further include a mobile handheld device 39 capable of reading information stored in the memory tags 24 of the trays 11 and reading information provided by read-only tags of sample vessels 3 and/or racks 12. Positioning the handheld device 39 in proximity to one tray 11 can enable wireless/contactless information transmission via radio signals, e.g., information contained in the memory tag 24 can be read so as to retrieve the mapping of the sample vessels 3 with respect to the array of vessel positions 35 of the tray 11. For this purpose, the handheld device 39 can comprise an output section 41 such as, but not limited to, a graphical display for outputting the position of the sample vessels, respectively, read from the memory tag 24 of the tray 11.

The handheld device 39 can further include an input section 40 for inputting an identification information related to a requested (to-be-located) sample vessel 3. In one embodiment, an identification of the to-be-located sample vessel 3 and/or an identification of a person from whom sample contained in the sample vessel 3 can be drawn can be input into the input section 40 of the handheld device 39.

In one embodiment, the handheld device 39 can be programmed by an application setting up the handheld device 39 to read the position information from the memory tags 24 of the trays 11 and to output a position of a to-be-located sample vessel 3 based on a request input into the handheld device 39. For this purpose, the handheld device 39 can include a controller which can be programmed according to the specific demands of the user. Accordingly, based on a user-input request, the position of a requested sample vessel 3 can be located on the corresponding tray 11.

In one embodiment, the position of the to-be-located sample vessel 3 can be graphically displayed in the output section 41, e.g., by displaying the array of vessel positions 35 of the corresponding tray 11 as given by all racks 12 loaded on the tray 11 and highlighting the position of the to-be-located sample vessel 3.

In one embodiment, the position of the to-be-located sample vessel 3 can be alphanumerically displayed in the output section 41, e.g., by displaying the numbers of a row and a column of the array of vessel positions 35 as given by all racks 12 loaded on the tray 11.

Furthermore, the handheld device 39 can display a direction towards the position of the to-be-located sample vessel 3 relative to an orientation of the handheld device 39 so that the user can be directed to the sample vessel 3.

Accordingly, by the handheld device 39, the position of any desired sample vessel 3 on a tray 11 can readily be determined, e.g., to selectively remove the sample vessel 3 from the tray 11.

While the system 1 can comprise panel 44 for displaying inventory information, in one use case, the handheld device 39 can be used to read the information of memory tags 24 of the trays 11 in the storing/retrieving device 2 and to provide the user with position information concerning individual sample vessels 3.

Figure 4:
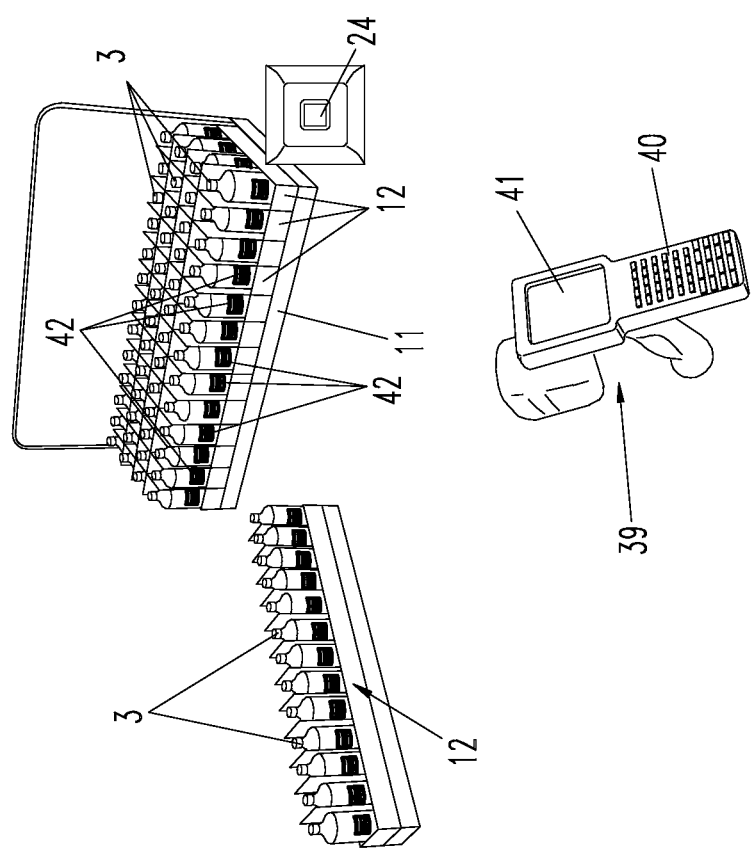
FIG. 4 illustrates a schematic view illustrating the use of a handheld device for locating sample vessels on a vessel holder kept in a long-time storage according to an embodiment of the present disclosure.

With reference to FIG. 4, in a use case, the handheld device 39 can be used to read the information of memory tags 24 of trays 11 outside the first and second storage compartments 4, 5, e.g., in a (long-time) storage compartment, e.g., providing a cooled environment, such as a refrigerator 43. Accordingly, the handheld device 39 can be used to locate samples and individual sample vessels 3, respectively, in trays 11 outside the first and second storage compartments 5, 6. When locating individual sample vessels 3, the handheld device 39 can be brought in close proximity to the refrigerator 43 so as to identify the tray 11 containing the to-be-requested sample vessel 3. As illustrated, the tray 11 can then be put out of the refrigerator 43 to remove the to-be-requested sample vessel 3. Furthermore, the inventory information of the tray 11 can be updated after removing the sample vessel 3 by reading read-only tags 42 (barcode labels) of the sample vessels 3 and optionally by reading read-only tags 42 of the racks 12 of the tray 11 and by writing information comprising position information of the residual sample vessels 3 with respect to the vessel positions 35 into the memory tag 24 of the tray 11. Accordingly, the inventory of the memory tag 24 of the tray 11 can be updated.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system for locating sample vessels, the system comprising:
   a vessel holder having an array of vessel positions for holding a plurality of sample vessels, wherein each vessel position in the vessel holder is capable of holding a sample vessel and wherein an information tag is attached to the vessel holder for storing and/or retrieving machine-readable information related to the positions of the plurality of sample vessels with respect to the array of vessel positions; and
   a device capable of reading information provided by the information tag, the device having an input section for inputting information related to a to-be-located sample vessel of the plurality of sample vessels and an output section for outputting a position of the to-be-located sample vessel of the plurality of sample vessels with respect to the array of vessel positions based on information stored in the information tag, and wherein the output section graphically displays the position of the to-be-located sample vessel with respect to the plurality of vessel positions of the vessel holder.

2. The system according to claim 1, wherein the device is a handheld device.

3. The system according to claim 1, wherein the device is a storing/retrieving device for storing and retrieving sample vessels.

4. The system according to claim 3, wherein the storing/retrieving device comprises a panel having the input section and the output section.

5. The system according to claim 3, wherein the storing/retrieving device comprises a reader/writer to read and/or write information on the information tag.

6. The system according to claim 3, wherein the storing/retrieving device comprises a controller comprising a database for storing inventory information with respect to each sample vessel in the plurality of sample vessels.

7. The system according to claim 6, wherein the inventory information is used to locate sample vessels in the plurality of sample vessels.

8. The system according to claim 7, wherein vessel holders holding the plurality of sample vessels are located in long-term storage compartment.

9. The system according to claim 1, wherein the vessel holder comprises a tray having a plurality of rack positions.

10. The system according to claim 9, wherein a plurality of racks are inserted and/or removed from the tray.

11. The system according to claim 10, wherein the information tag contains information of the sample vessels with respect to the vessel positions of the racks on the tray.

12. The system according to claim 9, wherein each rack comprises at least one sample vessel.

13. The system according to claim 1, further comprising, a sorting device for sorting sample vessels with respect to the plurality of vessel positions of the vessel holder.

14. The system according to claim 1, wherein the information tag is a RFID tag, a magnetic storage tag, a memory chip or combinations thereof.

15. The system according to claim 1, wherein the information tag is converted to a read-only tag.

16. The system according to claim 1, wherein the information tag converted to read-only by fusing a conductor, by encryption, by checksums or combinations thereof.

17. The system according to claim 1, wherein the information provided by the information tag is updated after the removal of one or more sample vessels from the vessel holder.

18. The system according to claim 1, further comprising, a first storage compartment; and a second storage compartment.

19. The system according to claim 18, wherein the first storage compartment stores sample vessels containing to-be-processed samples.

* * * * *